United States Patent
Bolduc

(10) Patent No.: US 8,092,519 B2
(45) Date of Patent: *Jan. 10, 2012

(54) ENDOVASCULAR ANEURYSM REPAIR SYSTEM

(75) Inventor: Lee Bolduc, Sunnyvale, CA (US)

(73) Assignee: Aptus Endosystems, Inc., Sunnyvale, CA (US)

(*) Notice: Subject to any disclaimer, the term of this patent is extended or adjusted under 35 U.S.C. 154(b) by 1496 days.

This patent is subject to a terminal disclaimer.

(21) Appl. No.: 11/166,411

(22) Filed: Jun. 24, 2005

(65) Prior Publication Data

US 2005/0240260 A1 Oct. 27, 2005

Related U.S. Application Data

(62) Division of application No. 10/271,334, filed on Oct. 15, 2002, now Pat. No. 6,960,217.

(60) Provisional application No. 60/333,937, filed on Nov. 28, 2001.

(51) Int. Cl.
*A61F 2/06* (2006.01)

(52) U.S. Cl. .................................... 623/1.36

(58) Field of Classification Search .............. 606/108, 606/151, 153, 157, 191, 194, 198, 213; 623/1.11–1.38; 128/898
See application file for complete search history.

(56) References Cited

U.S. PATENT DOCUMENTS

| | | | |
|---|---|---|---|
| 2,033,039 A | 3/1936 | Limpert | |
| 3,499,222 A | 3/1970 | Linkow et al. | |
| 3,686,740 A | 8/1972 | Shiley | |
| 3,799,172 A | 3/1974 | Szpur | |
| 4,140,126 A | 2/1979 | Choudhury | |
| 4,307,722 A | 12/1981 | Evans | |
| 4,580,568 A | 4/1986 | Gianturco | |
| 4,625,597 A | 12/1986 | Cast | |
| 4,781,682 A | 11/1988 | Patel | |
| 4,898,577 A | 2/1990 | Badger et al. | |
| 4,921,484 A | 5/1990 | Hillstead | |
| 4,990,151 A | 2/1991 | Wallsten | |
| 4,994,071 A | 2/1991 | MacGregor | |
| 5,030,204 A | 7/1991 | Badger et al. | |
| 5,042,707 A * | 8/1991 | Taheri | 606/213 |
| 5,071,407 A | 12/1991 | Termin et al. | |

(Continued)

FOREIGN PATENT DOCUMENTS

EP 0 321 912 12/1987

(Continued)

OTHER PUBLICATIONS

5mm Origin Tracker™ It Runs In Circles Around Staples, 1995 Advertising Literature.

(Continued)

*Primary Examiner* — Kevin T Truong
(74) *Attorney, Agent, or Firm* — Morrison & Foerster LLP

(57) ABSTRACT

Method and apparatus for implanting radially expandable prostheses in the body lumens rely on tacking or anchoring of the prostheses with separately introduced fasteners. The prostheses may be self-expanding or balloon expandable. After initial placement, a fastener applier system is introduced within the expanded prostheses to deploy a plurality of fasteners at least one prosthesis end, usually as each end of the prosthesis. The fasteners are usually helical fasteners which are delivered from a helical track in the fastener applier by rotation with a rotator wire. The fasteners will be applied singly, typically in circumferentially spaced-apart patterns about the interior of each end of the prosthesis.

9 Claims, 19 Drawing Sheets

U.S. PATENT DOCUMENTS

| | | |
|---|---|---|
| 5,104,399 A | 4/1992 | Lazarus |
| 5,192,314 A | 3/1993 | Daskalakis |
| 5,207,695 A | 5/1993 | Trout, III |
| 5,282,824 A | 2/1994 | Gianturco |
| 5,290,295 A | 3/1994 | Querals et al. |
| 5,318,525 A | 6/1994 | West et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,364,351 A | 11/1994 | Heinzelman et al. |
| 5,387,235 A | 2/1995 | Chuter |
| 5,456,713 A | 10/1995 | Chutter |
| 5,456,714 A | 10/1995 | Owen |
| 5,470,337 A | 11/1995 | Moss |
| 5,474,568 A | 12/1995 | Scott |
| 5,480,382 A | 1/1996 | Hammerslag et al. |
| 5,480,423 A | 1/1996 | Ravenscroft et al. |
| 5,489,295 A | 2/1996 | Piplani et al. |
| 5,531,686 A | 7/1996 | Lundquist et al. |
| 5,534,007 A | 7/1996 | St. Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A | 12/1996 | Bolduc et al. |
| 5,609,627 A | 3/1997 | Goicechea et al. |
| 5,626,613 A | 5/1997 | Schmieding |
| 5,628,788 A | 5/1997 | Pinchuk |
| 5,632,772 A | 5/1997 | Alcime et al. |
| 5,639,278 A | 6/1997 | Dercume et al. |
| 5,662,675 A | 9/1997 | Stockert et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | McDonald |
| 5,683,450 A | 11/1997 | Goicechea et al. |
| 5,693,084 A | 12/1997 | Chuter |
| 5,693,086 A | 12/1997 | Goicechea et al. |
| 5,700,269 A | 12/1997 | Pinchuk et al. |
| 5,702,365 A | 12/1997 | King |
| 5,702,408 A | 12/1997 | Wales et al. |
| 5,707,376 A | 1/1998 | Kavteladze et al. |
| 5,713,907 A | 2/1998 | Bogendijk et al. |
| 5,733,325 A | 3/1998 | Robinson et al. |
| 5,749,921 A | 5/1998 | Lenker et al. |
| 5,755,777 A | 5/1998 | Chuter |
| 5,762,458 A | 6/1998 | Wang et al. |
| 5,776,142 A | 7/1998 | Gunderson |
| 5,810,882 A | 9/1998 | Bolduc et al. |
| 5,814,016 A | 9/1998 | Valley et al. |
| 5,824,008 A | 10/1998 | Bolduc et al. |
| 5,824,041 A | 10/1998 | Lenker et al. |
| 5,830,221 A | 11/1998 | Stein et al. |
| 5,830,229 A | 11/1998 | Konya et al. |
| 5,843,160 A | 12/1998 | Rhodes |
| 5,855,565 A | 1/1999 | Bar-Cohen et al. |
| 5,855,598 A | 1/1999 | Pinchuk |
| 5,865,791 A | 2/1999 | Whayne |
| 5,876,432 A | 3/1999 | Lau et al. |
| 5,904,713 A | 5/1999 | Leschinsky |
| 5,906,619 A | 5/1999 | Olson et al. |
| 5,906,641 A | 5/1999 | Thompson et al. |
| 5,916,263 A | 6/1999 | Goicechea et al. |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 5,997,556 A | 12/1999 | Tanner |
| 6,016,810 A | 1/2000 | Ravenscroft |
| 6,024,763 A | 2/2000 | Lenker et al. |
| 6,070,589 A | 6/2000 | Keith et al. |
| 6,077,297 A | 6/2000 | Robinson et al. |
| 6,086,582 A | 7/2000 | Altman et al. |
| 6,123,722 A | 9/2000 | Fogarty et al. |
| 6,126,685 A | 10/2000 | Lenker et al. |
| 6,145,509 A | 11/2000 | Tanner |
| 6,146,339 A | 11/2000 | Biagtan et al. |
| 6,168,610 B1 | 1/2001 | Marin et al. |
| 6,203,550 B1 | 3/2001 | Olson |
| 6,203,568 B1 | 3/2001 | Lombardi et al. |
| 6,217,597 B1 | 4/2001 | Tanner |
| 6,248,118 B1 | 6/2001 | Tanner et al. |
| 6,258,119 B1 | 7/2001 | Hussein et al. |
| 6,270,516 B1 | 8/2001 | Tanner et al. |
| 6,273,858 B1 | 8/2001 | Fox et al. |
| 6,287,315 B1 | 9/2001 | Wijeratne et al. |
| 6,296,656 B1 | 10/2001 | Bolduc et al. |
| 6,302,906 B1 | 10/2001 | Goicoechea et al. |
| 6,309,403 B1 | 10/2001 | Minor et al. |
| 6,319,278 B1 | 11/2001 | Quinn |
| 6,336,933 B1 | 1/2002 | Parodi |
| 6,346,118 B1 | 2/2002 | Baker et al. |
| 6,371,919 B1 | 4/2002 | Tanner et al. |
| 6,409,757 B1 | 6/2002 | Trout, III et al. |
| 6,423,059 B1 | 7/2002 | Hanson et al. |
| 6,428,565 B1 | 8/2002 | Wisselink |
| 6,458,152 B1 | 10/2002 | Khosravi et al. |
| 6,468,260 B1 | 10/2002 | Bumbalough et al. |
| 6,482,224 B1 | 11/2002 | Michler et al. |
| 6,520,974 B2 | 2/2003 | Tanner et al. |
| 6,544,253 B1 | 4/2003 | Tanner |
| 6,562,051 B1 | 5/2003 | Bolduc et al. |
| 6,576,009 B2 | 6/2003 | Ryan et al. |
| 6,592,593 B1 * | 7/2003 | Parodi et al. .............. 606/108 |
| 6,592,615 B1 | 7/2003 | Marcade et al. |
| 6,607,555 B2 | 8/2003 | Patterson et al. |
| 6,652,572 B2 | 11/2003 | Kugler et al. |
| 6,719,174 B1 | 4/2004 | Swift |
| 6,730,119 B1 | 5/2004 | Smalling |
| 6,800,081 B2 | 10/2004 | Parodi |
| 6,878,164 B2 | 4/2005 | Kujawski et al. |
| 6,929,661 B2 | 8/2005 | Bolduc et al. |
| 6,960,217 B2 | 11/2005 | Bolduc |
| 7,081,129 B2 | 7/2006 | Chobotov |
| 7,128,754 B2 | 10/2006 | Bolduc |
| 7,306,623 B2 | 12/2007 | Watson |
| 7,491,232 B2 | 2/2009 | Bolduc et al. |
| 7,637,932 B2 | 12/2009 | Bolduc et al. |
| 7,823,267 B2 | 11/2010 | Bolduc |
| 7,828,838 B2 | 11/2010 | Bolduc et al. |
| 2002/0065485 A1 | 5/2002 | DuBois et al. |
| 2002/0099432 A1 | 7/2002 | Yee |
| 2002/0156365 A1 | 10/2002 | Tsekos |
| 2003/0018358 A1 | 1/2003 | Saadat |
| 2003/0100943 A1 | 5/2003 | Bolduc |
| 2003/0163085 A1 | 8/2003 | Tanner et al. |
| 2003/0233140 A1 | 12/2003 | Hartley et al. |
| 2004/0002731 A1 | 1/2004 | Aganon et al. |
| 2004/0054352 A1 | 3/2004 | Adams et al. |
| 2004/0093057 A1 | 5/2004 | Bolduc et al. |
| 2004/0127916 A1 | 7/2004 | Bolduc et al. |
| 2004/0260383 A1 | 12/2004 | Stelter et al. |
| 2005/0113906 A9 | 5/2005 | Bolduc et al. |
| 2005/0187613 A1 | 8/2005 | Bolduc |
| 2005/0240258 A1 | 10/2005 | Bolduc et al. |
| 2005/0240260 A1 | 10/2005 | Bolduc |
| 2006/0100640 A1 | 5/2006 | Bolduc et al. |
| 2006/0259125 A1 | 11/2006 | Peacock, III |
| 2007/0021829 A1 | 1/2007 | Bolduc et al. |
| 2007/0032860 A1 | 2/2007 | Brooks et al. |
| 2007/0073389 A1 | 3/2007 | Bolduc et al. |
| 2008/0065117 A1 | 3/2008 | Bolduc et al. |
| 2008/0065189 A1 | 3/2008 | Bolduc |
| 2008/0097489 A1 | 4/2008 | Goldfarb et al. |
| 2008/0132996 A1 | 6/2008 | Drasler et al. |
| 2009/0082852 A1 | 3/2009 | Bolduc et al. |
| 2010/0094400 A1 | 4/2010 | Bolduc et al. |

FOREIGN PATENT DOCUMENTS

| | | |
|---|---|---|
| EP | 0 663 184 | 1/1994 |
| EP | 1 369 098 A1 | 12/2003 |
| EP | 1 440 673 A1 | 7/2004 |
| FR | 2299548 | 1/1975 |

| JP | 2001-526574 A | 12/2001 |
| WO | WO 97/03616 | 2/1997 |
| WO | WO-98/53761 A1 | 12/1998 |
| WO | WO 99/53845 | 10/1999 |
| WO | WO 00/16701 | 3/2000 |
| WO | WO-00/35350 A1 | 6/2000 |
| WO | WO-03/079935 A1 | 10/2003 |
| WO | WO-2005/044073 A2 | 5/2005 |
| WO | WO-2005-044073 A3 | 5/2005 |

OTHER PUBLICATIONS

"The Spiral Tracker: A New Technique for Stabilizing Prosthetic Mesh in Laparoscopic Hernia Repair", Nov. 1995 *Surgical Rounds*.

"Laparoscopic Surgery", *MedPro Month* Oct. 1995, p. 190.

"Assisted TAPP Procedure", Newman III et al., Circa 1995.

"Extraperitoneal Endoscopic Burch Repair Using a Tacker Mesh Technique", Hatchett et al., Circa 1995.

Non-final Office Action mailed May 18, 2004, for U.S. Appl. No. 10/271,334, filed on Oct. 15, 2002, 8 pages.

Examiners Interview Summary mailed Feb. 11, 2005, for U.S. Appl. No. 10/271,334, filed on Oct. 15, 2002, 1 page.

Non-Final Office Action mailed Oct. 6, 2008, for U.S. Appl. No. 11/540,427, filed on Sep. 29, 2006, 9 pages.

Final Office Action mailed Jul. 21, 2009, for U.S. Appl. No. 11/540,427, filed on Sep. 29, 2006, 8 pages.

Non-Final Office Action mailed May 20, 2010, for U.S. Appl. No. 11/978,752, filed Oct. 30, 2007, 5 pages.

Final Office Action mailed Dec. 22, 2010, for U.S. Appl. No. 11/978,752, filed Oct. 30, 2007, 6 pages.

Non-Final Office Action mailed Sep. 3, 2010, for U.S. Appl. No. 11/978,753, filed Oct. 30, 2007, 7 pages.

Non-Final Office Action mailed Jan. 27, 2006, for U.S. Appl. No. 10/669,881, filed Sep. 24, 2003, 5 pages.

Final Office Action mailed Jan. 25, 2008, for U.S. Appl. No. 10/669,881, filed Sep. 24, 2003, 7 pages.

Notice of Allowance mailed Oct. 8, 2008, for U.S. Appl. No. 10/669,881, filed Sep. 24, 2003, 6 pages.

Notice of Allowance mailed Mar. 9, 2010, for U.S. Appl. No. 11/254,444, filed Oct. 20, 2005, 6 pages.

Notice of Allowance mailed Jun. 29, 2010, for U.S. Appl. No. 11/254,444, filed Oct. 20, 2005, 6 pages.

Non-Final Office Action mailed Oct. 1, 2009, for U.S. Appl. No. 11/254,619, filed Oct. 20, 2005, 5 pages.

Final Office Action mailed Jun. 30, 2010, for U.S. Appl. No. 11/254,619, filed Oct. 20, 2005, 10 pages.

Non-Final Office Action mailed Feb. 3, 2011, for U.S. Appl. No. 11/254,619, filed Oct. 20, 2005, 8 pages.

Non-Final Office Action mailed Mar. 30, 2009, for U.S. Appl. No. 11/254,950, filed on Oct. 20, 2005, 5 pages.

Notice of Allowance mailed Feb. 26, 2010, for U.S. Appl. No. 11/254,950, filed on Oct. 20, 2005, 4 pages.

Notice of Allowance mailed Jun. 22, 2010, for U.S. Appl. No. 11/254,950, filed on Oct. 20, 2005, 4 pages.

Non-Final Office Action mailed May 14, 2008, for U.S. Appl. No. 11/255,116, filed Oct. 20, 2005, 14 pages.

Notice of Allowance mailed Aug. 10, 2009, for U.S. Appl. No. 11/255,116, filed Oct. 20, 2005, 4 pages.

Non-Final Office Action mailed Sep. 1, 2010, for U.S. Appl. No. 11/488,305, filed Jul. 18, 2006, 7 pages.

International Search Report mailed Jul. 8, 2008, for PCT Patent Application No. PCT/US2006/033747, filed on Aug. 29, 2006, published on Apr. 26, 2007, as WO 2007/046954, 2 pages.

Written Opinion mailed Jul. 8, 2008, for PCT Patent Application No. PCT/US2006/033747, filed on Aug. 29, 2006, published on Apr. 26, 2007, as WO 2007/046954, 3 pages.

International Search Report mailed on Feb. 24, 2006, for PCT Patent Application No. PCT/US2004/029402, filed on Sep. 10, 2004, published on Apr. 14, 2005, as WO 2005/032333, 3 pages.

Written Opinion mailed on Feb. 24, 2006, for PCT Patent Application No. PCT/US2004/029402, filed on Sep. 10, 2004, published on Apr. 14, 2005, as WO 2005/032333, 3 pages.

International Preliminary Report on Patentability mailed on Jul. 10, 2006, for PCT Patent Application No. PCT/US2004/029402, filed on Sep. 10, 2004, published on Apr. 14, 2005, as WO 2005/032333, 3 pages.

International Search Report mailed on Mar. 30, 2007, for PCT Patent Application No. PCT/US2006/033741, filed on Aug. 29, 2006, published on Apr. 26, 2007, as WO 2007/046953, 2 pages.

Written Opinion mailed on Mar. 30, 2007, for PCT Patent Application No. PCT/US2006/033741, filed on Aug. 29, 2006, published on Apr. 26, 2007, as WO 2007/046953, 4 pages.

International Preliminary Examination Report mailed on Jul. 28, 2007, for PCT Patent Application No. PCT/US2006/033741, filed on Aug. 29, 2006, published on Apr. 26, 2007, as WO 2007/046953, 5 pages.

International Search Report mailed on Aug. 15, 2007, for PCT Patent Application No. PCT/US2006/033748, filed on Aug. 29, 2006, published on May 10, 2007, as WO 2007/053233, 3 pages.

Written Opinion mailed on Aug. 15, 2007, for PCT Patent Application No. PCT/US2006/033748, filed on Aug. 29, 2006, published on May 10, 2007, as WO 2007/053233, 5 pages.

International Preliminary Report on Patentability mailed on Jun. 18, 2008, for PCT Patent Application No. PCT/US2006/033748, filed on Aug. 29, 2006, published on May 10, 2007, as WO 2007/053233, 7 pages.

International Search Report mailed on Aug. 15, 2007, for PCT Patent Application No. PCT/US06/033749, filed on Aug. 29, 2006, published on Apr. 26, 2007, as WO 2007/046955, 3 pages.

Written Opinion mailed on Aug. 15, 2007, for PCT Patent Application No. PCT/US06/033749, filed on Aug. 29, 2006, published on Apr. 26, 2007, as WO 2007/046955, 5 pages.

International Preliminary Report on Patentability mailed on Jun. 18, 2008, for PCT Patent Application No. PCT/US06/033749, filed on Aug. 29, 2006, published on Apr. 26, 2007, as WO 2007/046955, 6 pages.

* cited by examiner

ENDOVASCULAR ANEURYSM REPAIR SYSTEM

RELATED APPLICATION

This application is a divisional of U.S. patent application Ser. No. 10/271,334 filed Oct. 15, 2002, now U.S. Pat. No. 6,960,217 which claims the benefit of U.S. provisional application Ser. No. 60/333,937 filed 28 Nov. 2001.

BACKGROUND OF THE INVENTION

The invention relates generally to the attachment of a vascular prosthesis to a native vessel, and in particular, to a method and system of devices for the repair of diseased and/or damaged sections of a vessel.

Description of Related Art. The weakening of a vessel wall from damaged or diseased can lead to vessel dilatation and the formation of an aneurysm. Left untreated, an aneurysm can grow in size and will eventually rupture.

For example, aneurysms of the aorta primarily occur in abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic graft, made either in a straight of bifurcated configuration, is installed and then permanently attached and sealed to the ends of the native vessel by suture. The prosthetic grafts for these procedures are usually unsupported woven tubes and are typically made from polyester, ePTFE or other suitable materials. The grafts are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co morbidities.

Endovascular aneurysm repair has been introduced to overcome the problems associated with open surgical repair. The aneurysm is bridged with a vascular prosthesis, which is placed intraluminally. Typically these prosthetic grafts for aortic aneurysms are delivered collapsed on a catheter through the femoral artery. These grafts are usually designed with a fabric material attached to a metallic scaffolding (stent) structure, which expands or is expanded to contact the internal diameter of the vessel. Unlike open surgical aneurysm repair, intraluminally deployed grafts are not sutured to the native vessel, but rely on either barbs extending from the stent, which penetrate into the native vessel during deployment, or the radial expansion force of the stent itself is utilized to hold the graft in position. These graft attachment means do not provide the same level of attachment when compared to suture and can damage the native vessel upon deployment.

Accordingly, there is a need for an endovascular aneurysm repair system that first provides a prosthetic graft, which can adapt to changes in aneurysm morphology and be deployed without damaging the native vessel and second, a separate endovascular fastening system that provides permanent graft attachment to the vessel wall.

SUMMARY OF THE INVENTION

The methods and apparatus for implanting radially expandable prostheses is the body lumens are described. In particular, the present invention provides improved methods and systems for implanting vascular stents and stent-grafts into blood vessels, including both arterial and venous systems. In the exemplary embodiments, stent-grafts are placed in vasculature to reinforce aneurysms, particularly abdominal aortic aneurysms.

In the first aspect of the present invention, a radially expandable prosthesis is placed in a body lumen by first expanding at least one scaffold of the prosthesis at or near an implantation site within the body lumen, e.g., at or from vasculature on one side of an aneurysm. After expanding the scaffold of the prosthesis, a plurality of fasteners are introduced through the prosthesis in the region in the scaffold to anchor the scaffold in place. The scaffold may be elastic, typically comprised of a shape memory alloy elastic stainless steel, or the like. For elastic scaffolds, expanding typically comprises releasing the scaffolding from constraint to permit the scaffold to self-expand at the implantation site. The constraint may be radial constraint, i.e., placement of a tubular catheter, delivery sheath, or the like over the scaffold in order to maintain the scaffold in a radially reduced configuration. Expansion is then achieved by pulling back on the catheter sheath to permit the scaffold to return to its larger diameter configuration. Alternatively, the scaffold may be constrained in an axially elongated configuration, e.g., by attaching either end of the scaffold to an internal tube, rod, catheter or the like, to maintain the scaffold in the elongated, reduced diameter configuration. The scaffold may then be released from such axial constraint in order to permit self-expansion.

Alternatively, the scaffold may be formed from a malleable material, such as malleable stainless steel of other metals. Expansion may then comprise applying a radially expansive force within the scaffold to cause expansion, e.g., inflating a scaffold delivery catheter within the side of the scaffolding order to affect the expansion.

The vascular prosthesis may have a wide variety of conventional configurations. In the preferred placement of the vascular stent-graft, prosthesis would typically comprise a fabric other blood semi-impermeable flexible barrier which is supported by a scaffold, typically in the form of a stent. A stent can have any conventional stent configurations, such as zigzag, serpentine, expanding diamond, or combinations thereof. The stent structure may extend the entire length of the graft, and in some instances will be longer than the fabric components of the graft. Alternatively, the stent will cover only a small portion of the prosthesis, e.g., being present on at 1, 2, or 3 ends. The stent may have three or more ends when it is configured to treat bifurcated vascular regions, such as the treatment of abdominal aortic aneurysms when the stent graft extends into the iliac arteries. In certain instances, the stents may be spaced apart along the entire length, or at least a major portion of the entire length, of the stent-graft, where individual stent structures are not connected to each other directly, but rather connected to the fabric or other flexible component of the graft.

Introduction of the fasteners will typically be effected after the prosthesis has been initially placed. That is initial placement will be achieved by self-expansion or balloon expansion, after which the prosthesis is secured or anchored in place by the introduction of a plurality of individual fasteners, preferably helical fasteners which are rotated and "screwed into" the prosthesis and vessel wall. Fasteners may be placed through the fabric only, i.e., avoiding the scaffold structure. Alternately, the fasteners can be introduced into and through portions of the scaffold structure, optionally through receptacles or apertures which have been specially configured to receive the fasteners. In some cases, of course, fasteners will be introduced both through the fabric and through of over the scaffold structure.

In the exemplary embodiment, the fasteners are helical fasteners, which are introduced singly, i.e., one at a time, in a circumferentially spaced-apart pattern over an interior wall of the prosthesis. Usually, the fasteners will be introduced using a fastener applier which carries a single fastener. Fastener appliers which carry a single fastener can have a lower profile and may be more effective and less traumatic than fastener appliers which carry multiple fasteners. The present invention, however, does contemplate that in certain embodiments the fastener applier may carry multiple fasteners. Moreover, the fastener applier may simultaneously deploy multiple fasteners in the preferred circumferentially spaced-apart space pattern described above. Usually, from 2-12 fasteners will be applied at each end of the prosthesis to be anchored. The 2-12 fasteners will usually be applied in a single circumferentially space-apart row that may be applied in more than one row with individual fasteners being axially aligned or circumferentially staggered. In a preferred embodiment, the intraluminal fastener applier of the present invention comprises a guide component and an applier component. The guide component, for example, comprises a tubular body having a deflectable distal tip and, optionally, a stabilizer for holding the deflected tip against a location in the graft to which the fastener is to be applied. The applier component is insertable through a lumen of the guide component and carries at least a single helical or other fastener. A rotation driver is provided for rotating and advancing the helical fastener so that it penetrates the graft and underlying vessel wall to anchor the graft firmly in place.

BRIEF DESCRIPTION OF THE DRAWINGS

The invention will be understood from the following detailed description of preferred embodiments, taken in conjunction with the accompanying drawings, wherein.

DETAILED DESCRIPTION OF THE INVENTION

Figure 1:
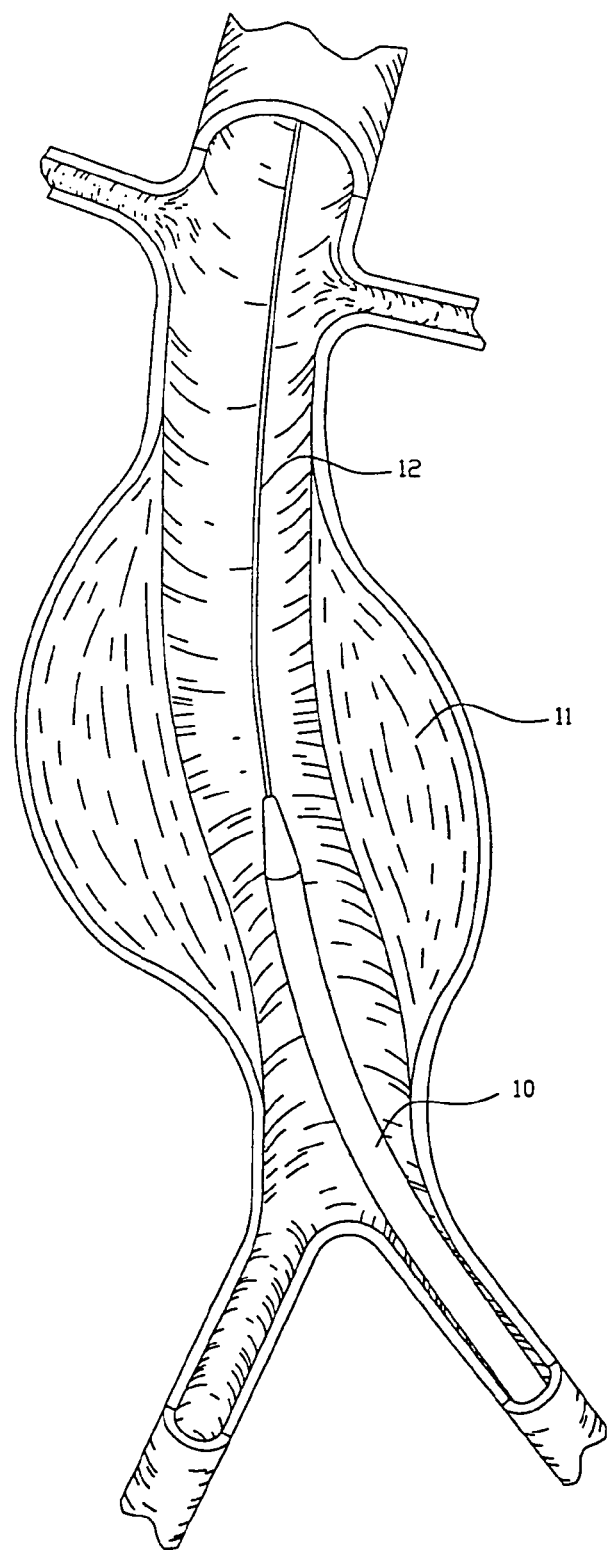
FIG. 1 is a perspective view of one embodiment of an endovascular graft delivery device shown positioned within an abdominal aortic aneurysm.
Figure 2:
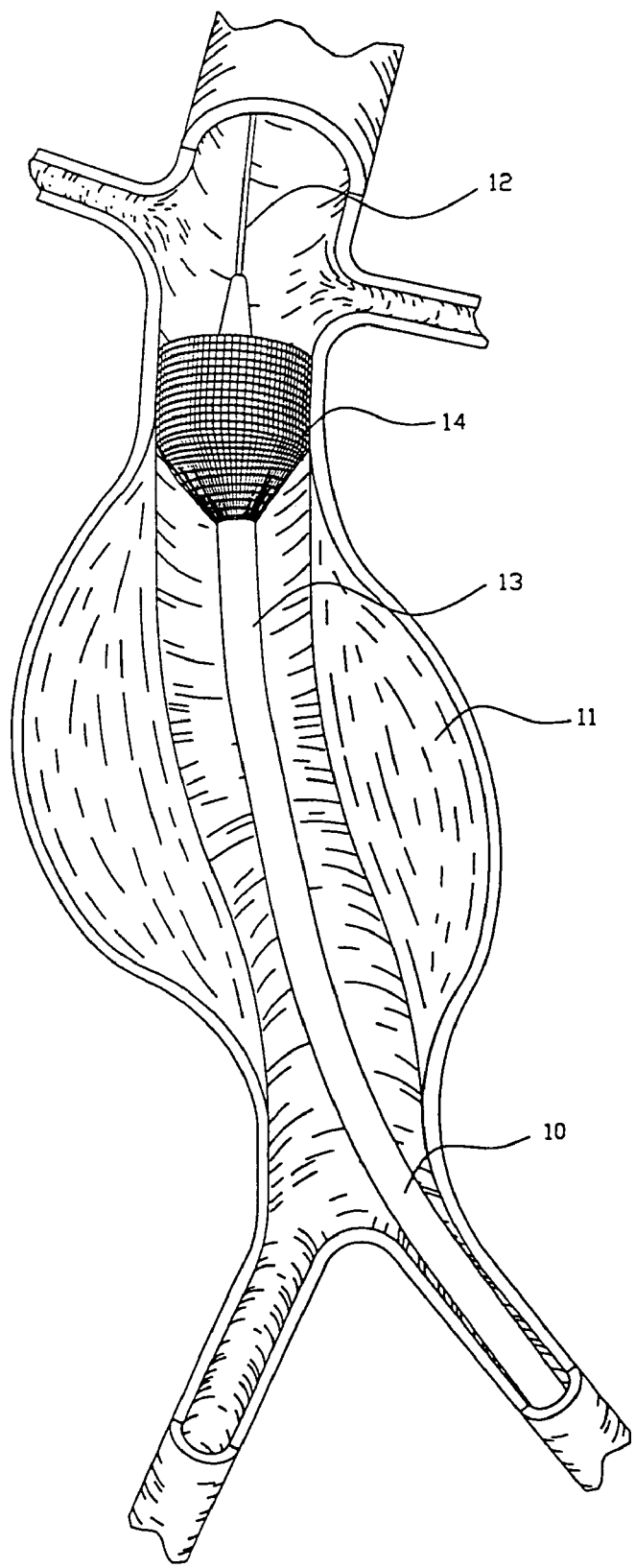
FIG. 2 is a perspective view of one embodiment the deployment of an endovascular graft within the aneurysm of FIG. 1.
Figure 3:
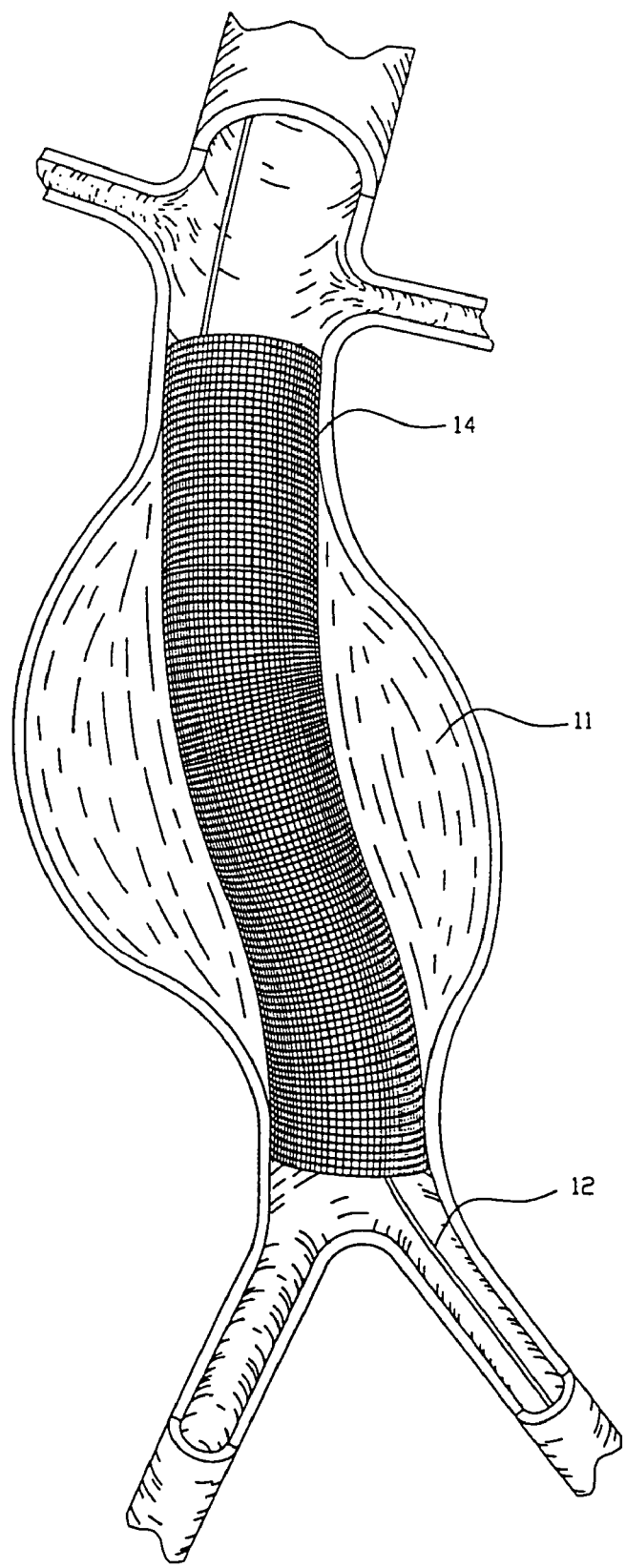
FIG. 3 is a perspective view of a fully deployed straight endovascular graft of FIG. 2.
Figure 4:
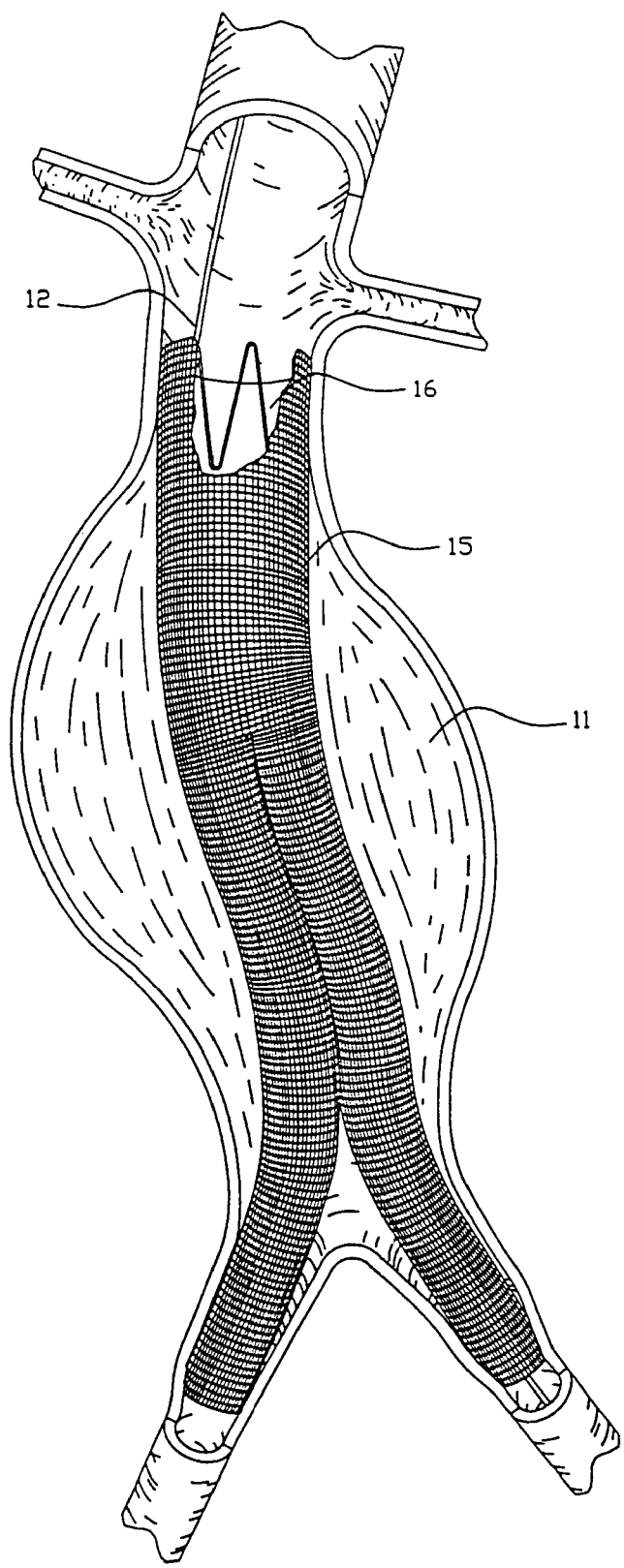
FIG. 4 is a perspective view of a fully deployed bifurcated endovascular graft broken away to show an anchoring scaffold at one end.
Figure 5:
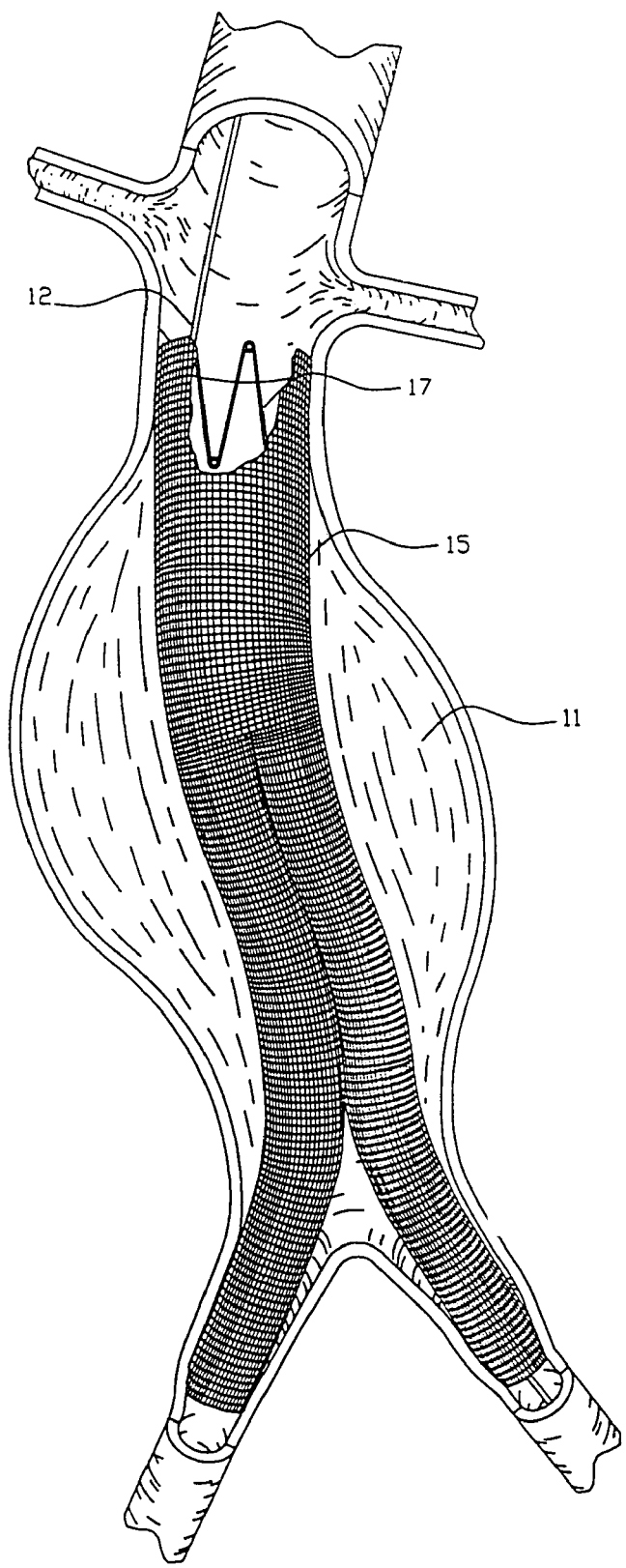
FIG. 5 is a perspective view similar to FIG. 5 showing an alternative scaffold structure.
Figure 6:
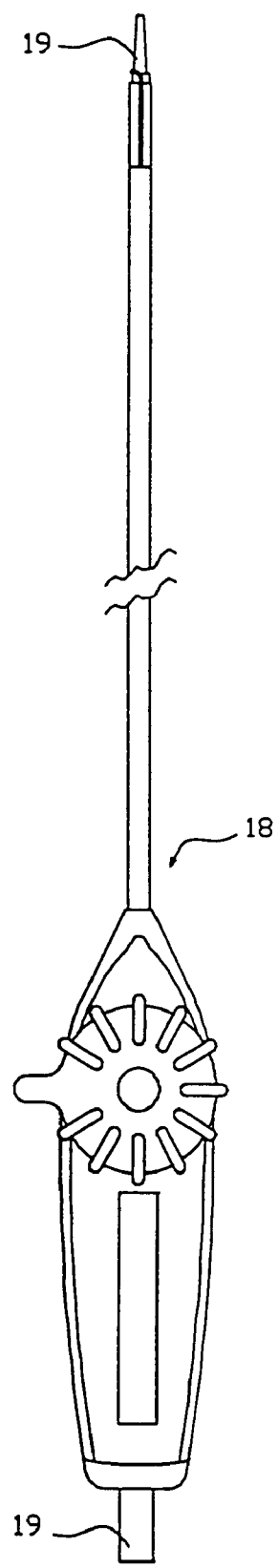
FIG. 6 is a perspective view showing one embodiment of a device for directing the fastener applier.
Figure 7:
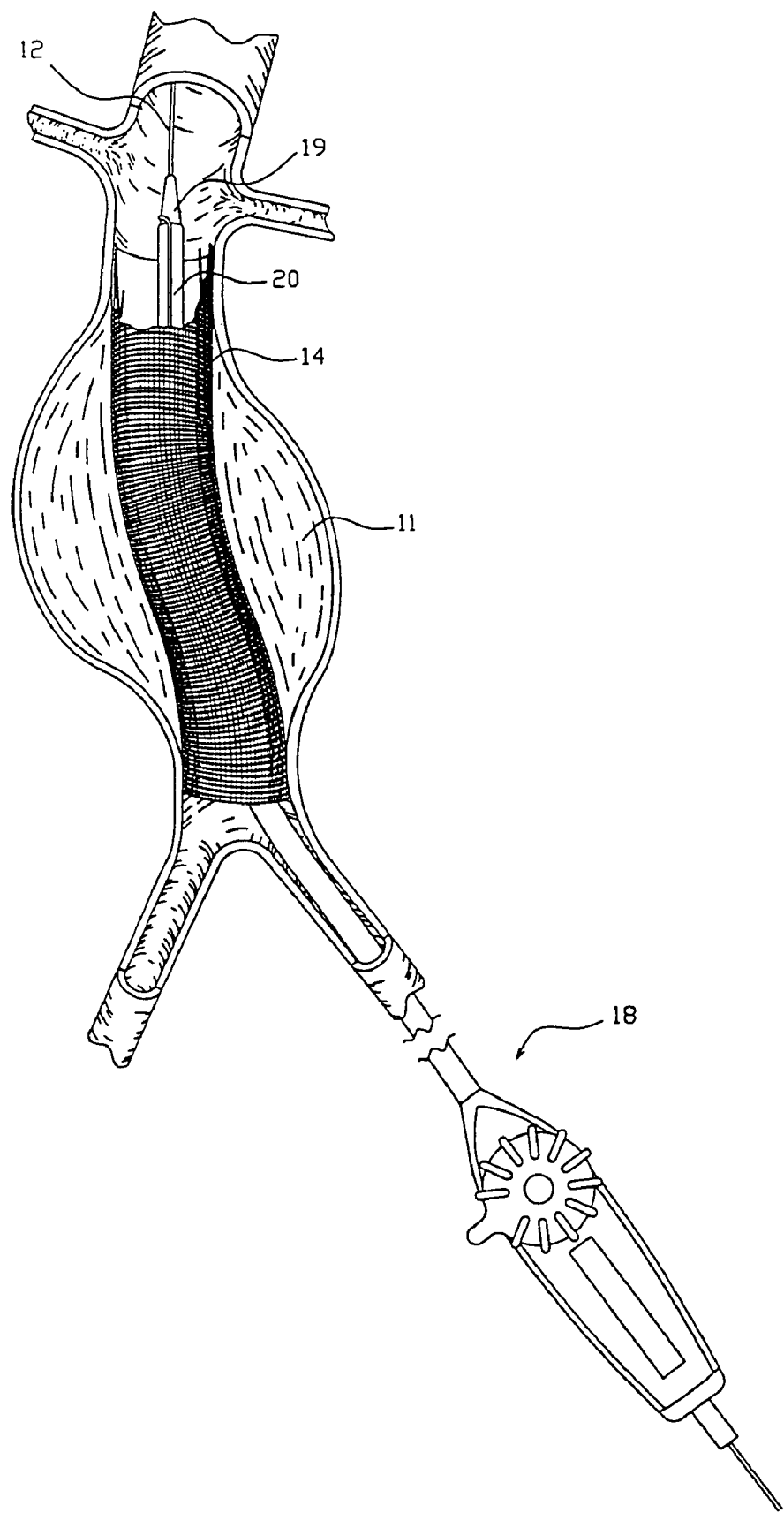
FIG. 7 is a perspective view showing the device of FIG. 6 upon insertion within the deployed endovascular graft of FIG. 3 with both the graft and scaffolding broken away.
Figure 8:
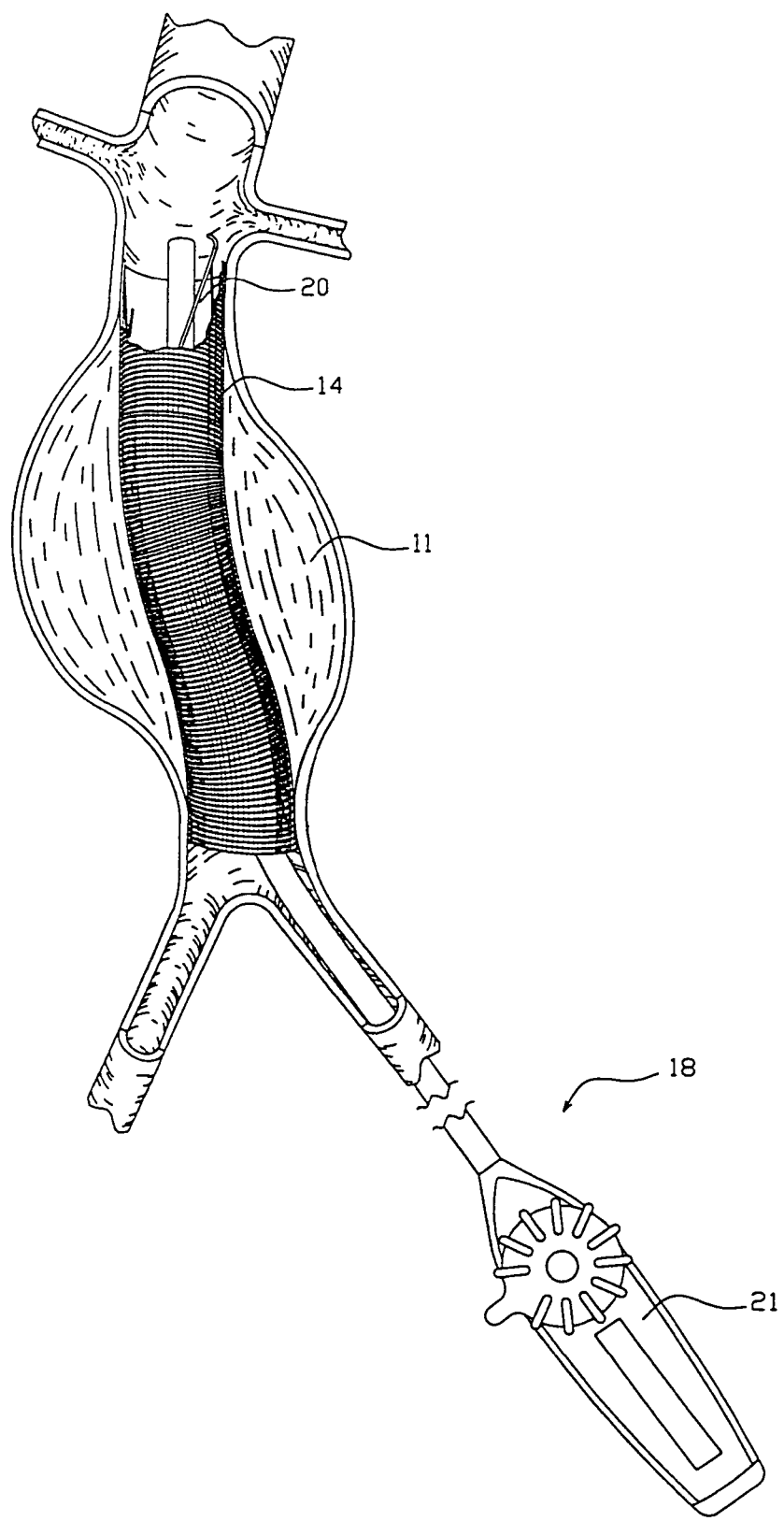
FIG. 8 is a perspective view of the device of FIG. 6 showing activation of one embodiment of a stabilizing device attached to the directing device.
Figure 9:
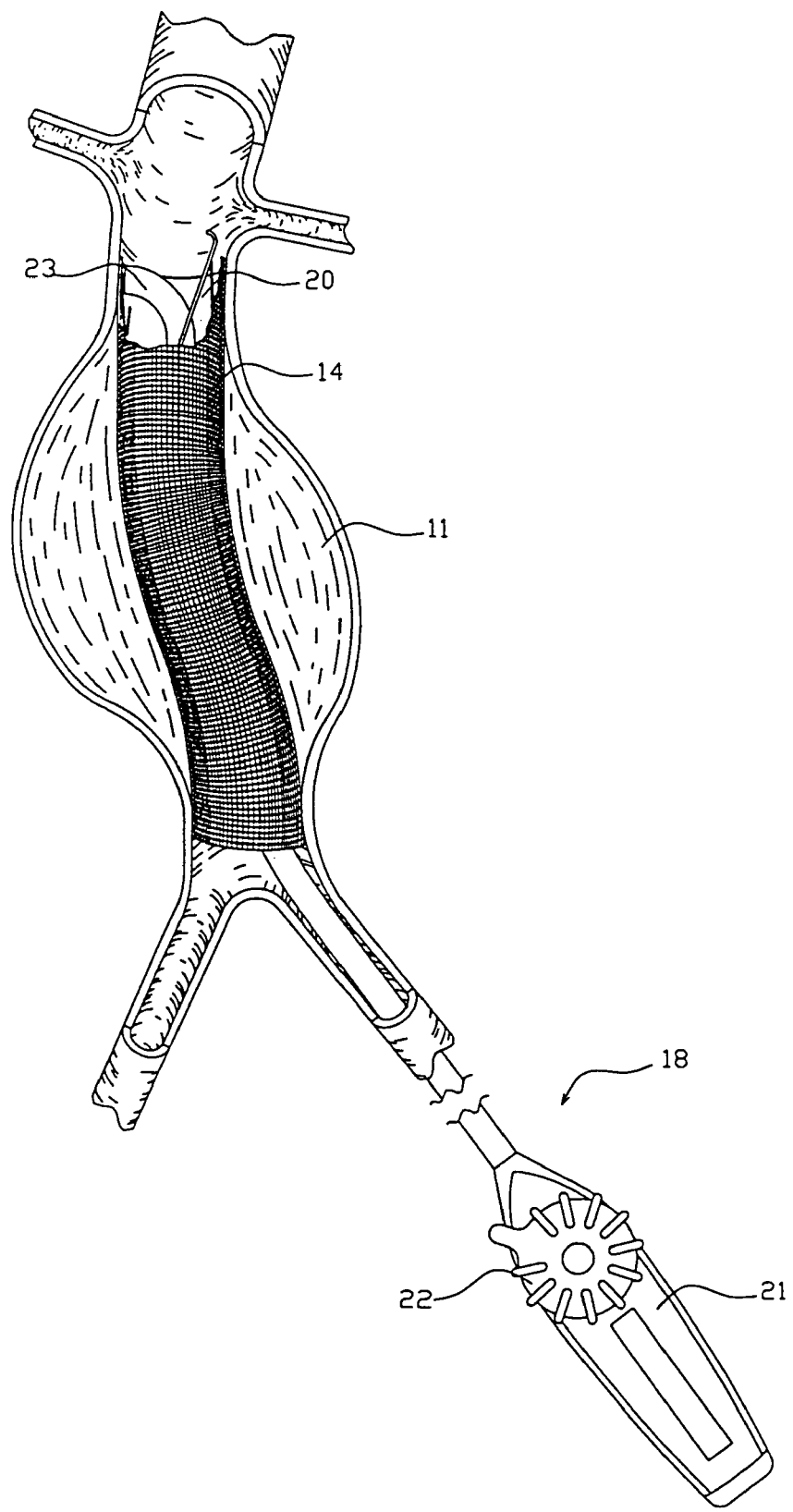
FIG. 9 is a perspective view of the control assembly in FIG. 8 articulating the directing device of FIG. 6.
Figure 10:
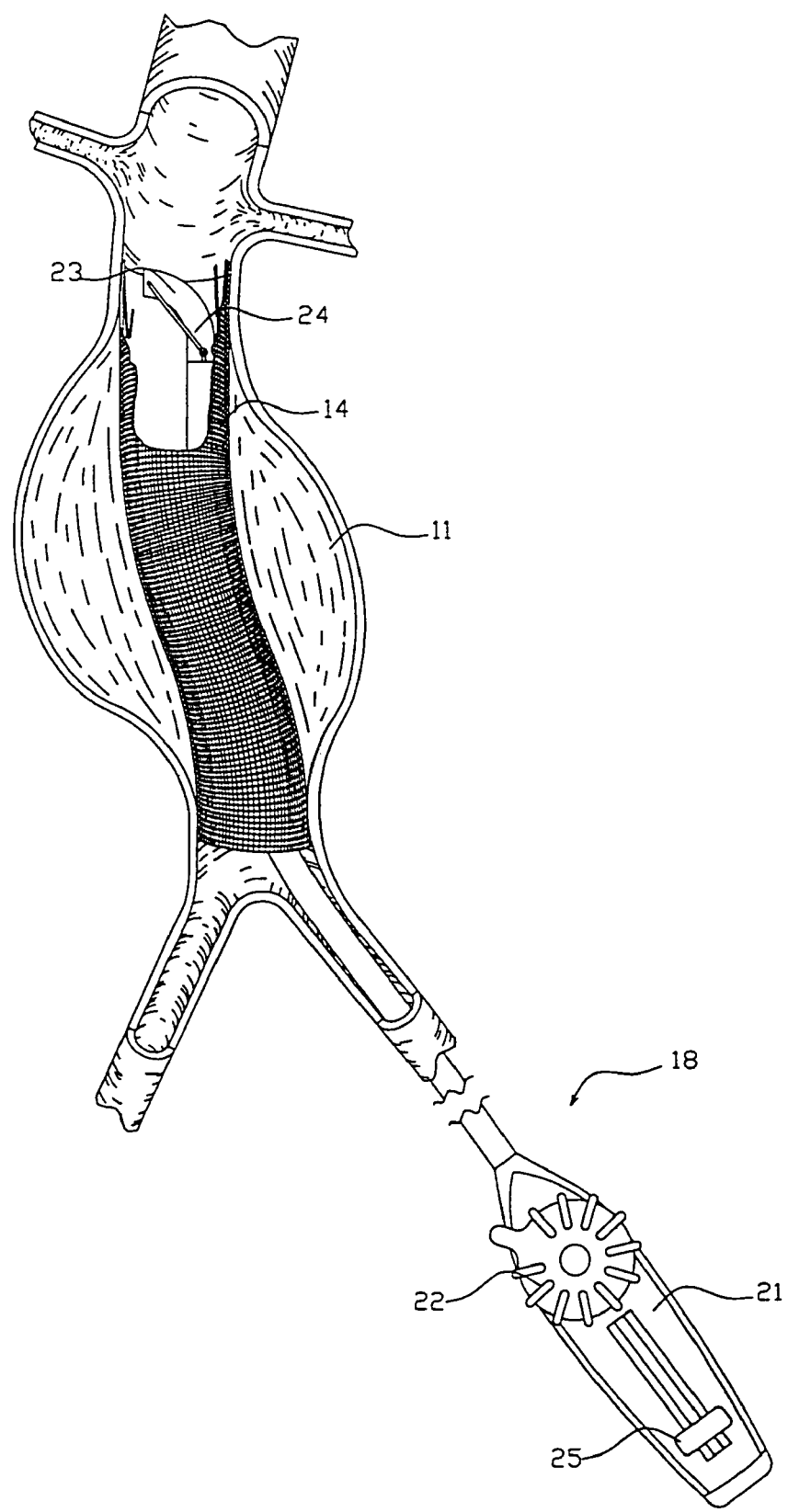
FIG. 10 is a perspective view of an alternative embodiment of the stabilization device of FIG. 8.
Figure 11:
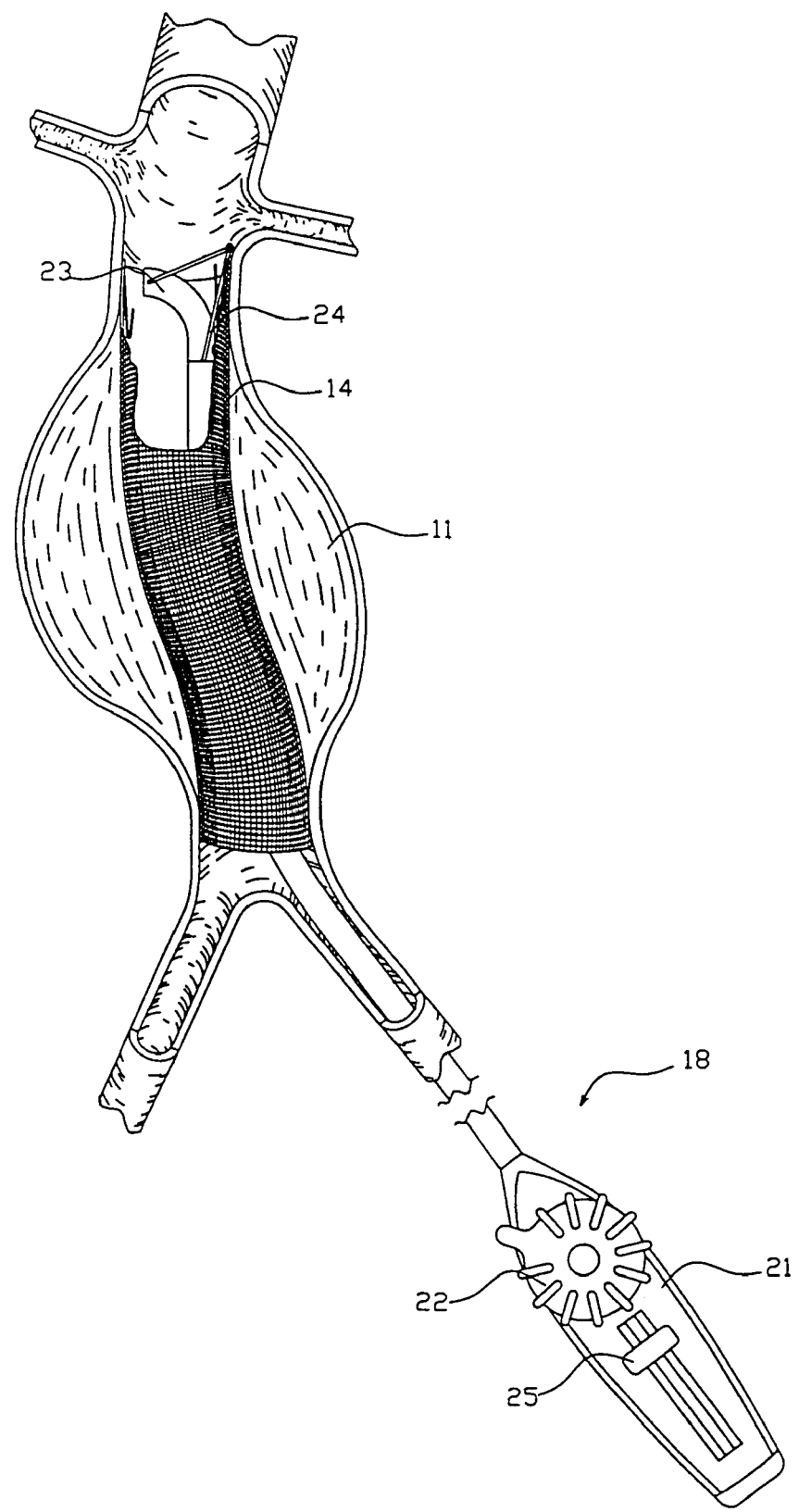
FIG. 11 is a perspective view showing the activation of the alternative stabilization device of FIG. 10.
Figure 12:
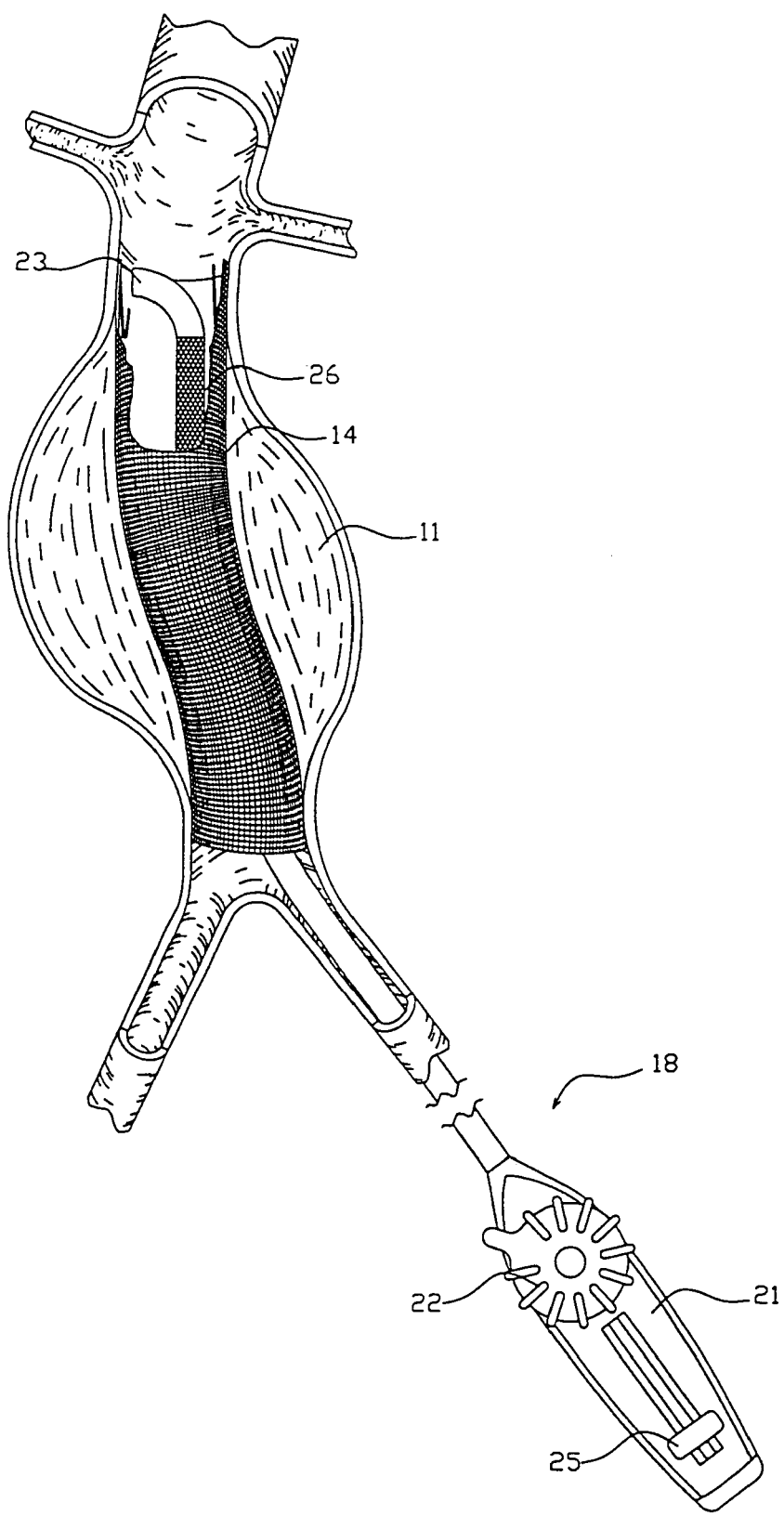
FIG. 12 is a perspective view showing another embodiment of the stabilization device of FIG. 8.
Figure 13:
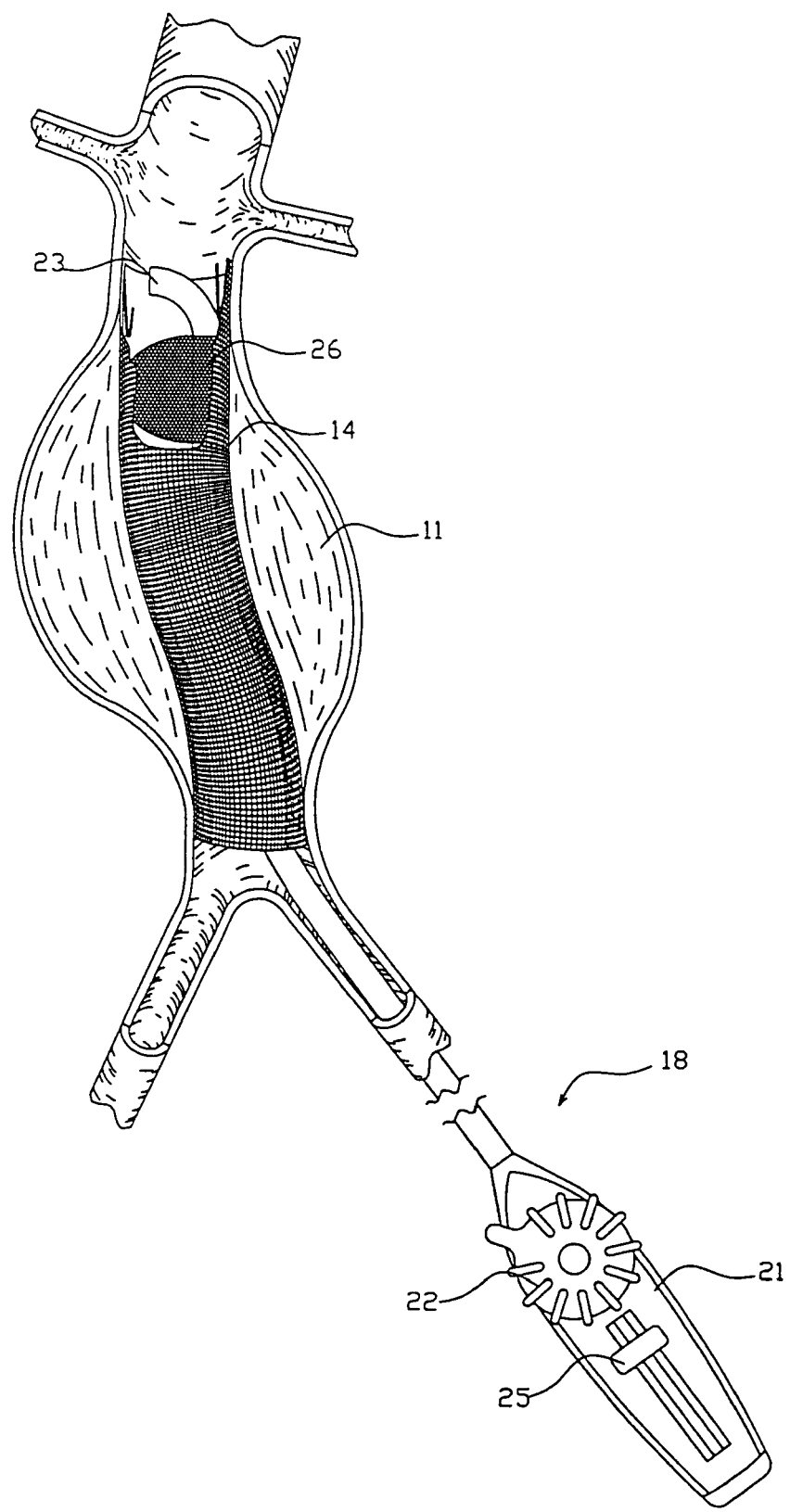
FIG. 13 is a perspective view showing activation of the stabilization device of FIG. 12.

FIG. 1 depicts an endovascular graft delivery catheter 10 being positioned within an abdominal aortic aneurysm 11 over a guidewire 12. FIG. 2 depicts the initial stage of graft deployment within a vessel. The delivery catheter 10 has a movable cover 13 over the graft. When the cover is pulled proximally the graft 14 expands to contact the internal walls of the vessel. It is contemplated that the graft could be self-expanding or utilize an expanding member such as a balloon or mechanical expander. The process of graft deployment is continued until the graft is fully deployed within the vessel. It is contemplated that the graft could be in either a straight or bifurcated form. FIG. 3 depicts a completely deployed straight graft 14 and FIG. 4 depicts a completely deployed bifurcated graft 15. The guidewire 11 used to deliver and position the graft remains within the vessel for access of the fastener attachment system. One embodiment of the graft scaffolding 16 (stent) is illustrated in the area broke away in FIG. 4. The stent is in the form of a simple zigzag pattern, however it is contemplated that the stent design could involve more complex patterns 17 as depicted in FIG. 5. Although only one stent structure within the graft is depicted, in FIGS. 4 and 5, it is contemplated that multiple independent stent structures could be incorporated into the graft. 1391 FIG. 6 depicts one embodiment of the directing device 18 with an obturator 19 positioned within the lumen of the directing device and extending past the distal of the tip of the directing device. The obturator has a lumen to allow for delivery over a guidewire. FIG. 7 depicts the directing device being positioned within the deployed endovascular graft over a Quidewire 12. The directing device has an incorporated stabilizing device 20 to aid in maintaining position of the directing device within the vessel. In one embodiment, the stabilizing device 20 is spring-loaded and is positioned for use when the obturator in the directing device is removed FIG. 8. The directing device is activated though a control assembly 21 as seen in FIG. 8. In one embodiment the control assembly 21 features a movable wheel or lever 22, which deflects the distal tip 23 of the directing device 18 to the desired location as seen in FIG. 9. It is contemplated that the control assembly for the directing device could be activated mechanically, electrically, hydraulically or pneumatically. The control assembly has a through lumen to allow for the passage of the obturator and fastener applier. FIG. 10 depicts another embodiment the stabilizing device as a movable strut assembly 24. The movable strut assembly is activated through a lever 25 on the control assembly FIG. 11. In both embodiments (FIGS. 7 and 10) the stabilizing device is distal to the end of the directing device. In another embodiment the stabilizing device could be in the form of an expandable member 26 adjacent to the distal tip of the directing device FIG. 12. In one embodiment, the expandable member 26 is shown activated through a lever 25 on the control assembly FIG. 13. However it also contemplated that this type of stabilizing device could also be inflatable. In all embodiments the stabilizing device could be use to stabilize the directing member either concentrically or eccentrically within the vessel.

In another embodiment of the invention a separate tubular device could be used in cooperation with the directing device and to access the vessel. This separate tubular device could incorporate the stabilizing devices used above with the directing device.

Figure 14A:
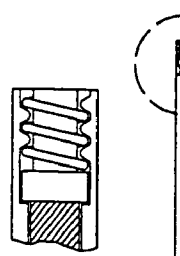
FIG. 14 is one embodiment of the fastener applier.
Figure 14:
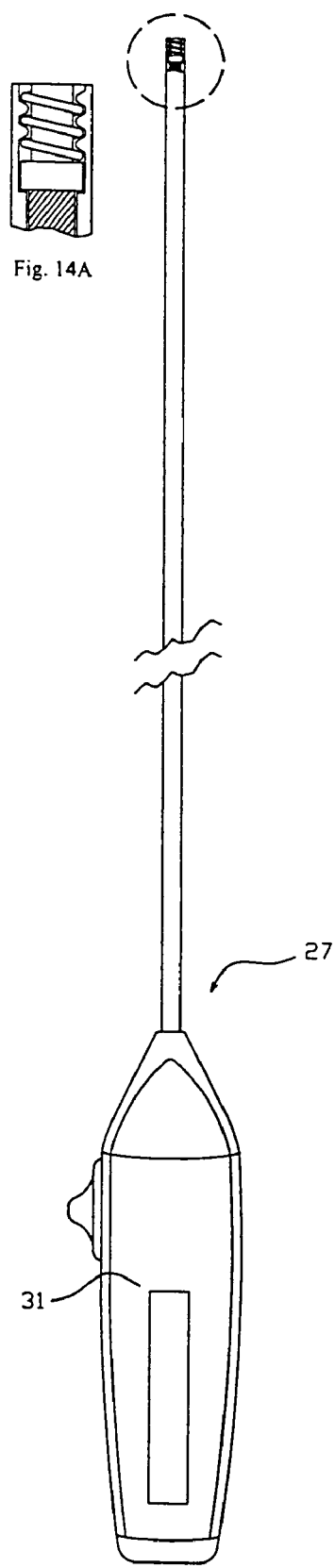
Figure 15:
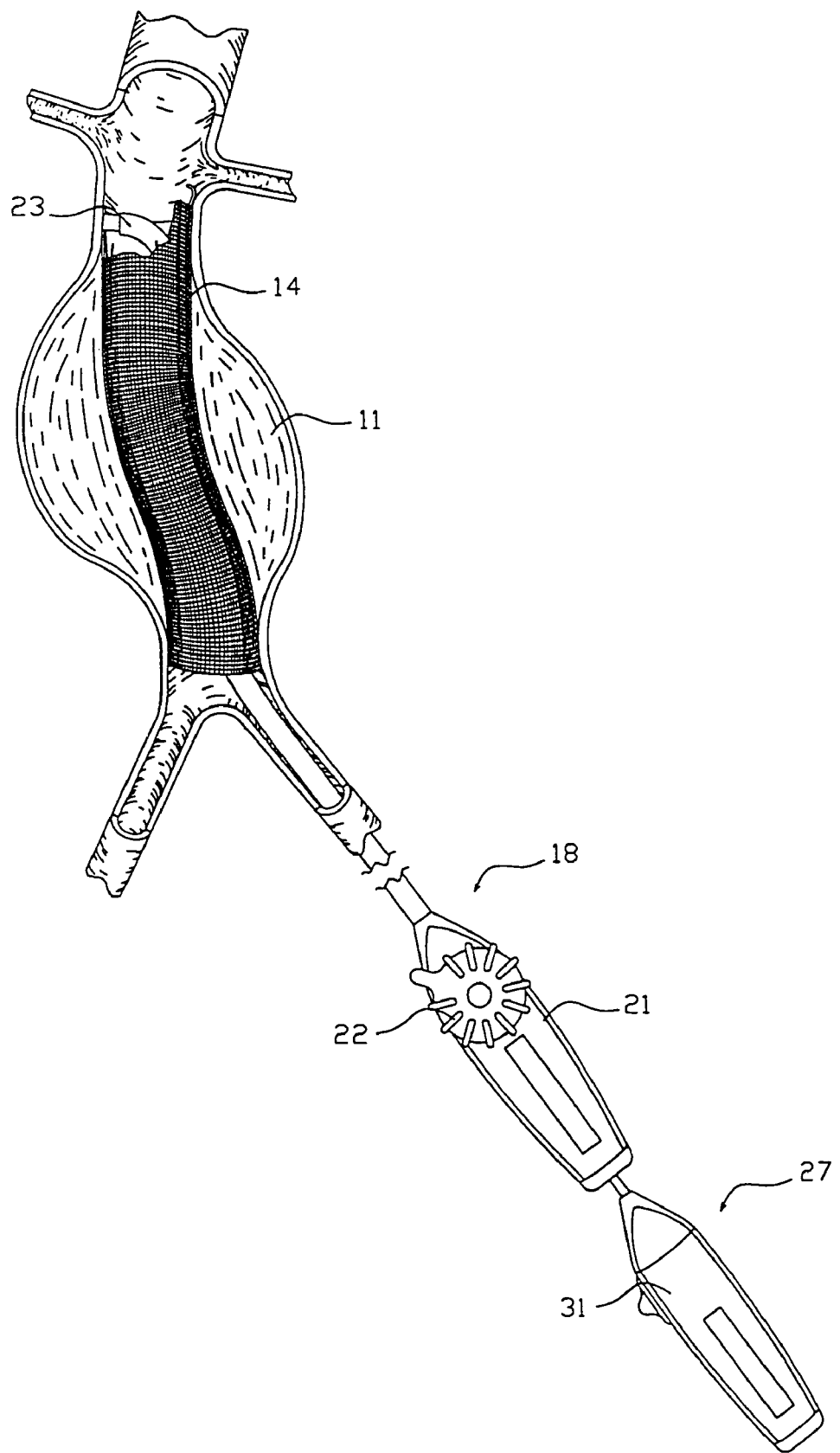
FIG. 15 is a perspective view of the fastener applier of FIG. 14 being positioned within directing device of FIG. 6.

FIG. 14 depicts one embodiment of the fastener applier 27. FIG. 14A is a detail view of the distal end of the fastener applier. FIG. 15 depicts the fastener applier being positioned through the lumen of the directing device to the site where a fastener will be installed.

Figure 16:
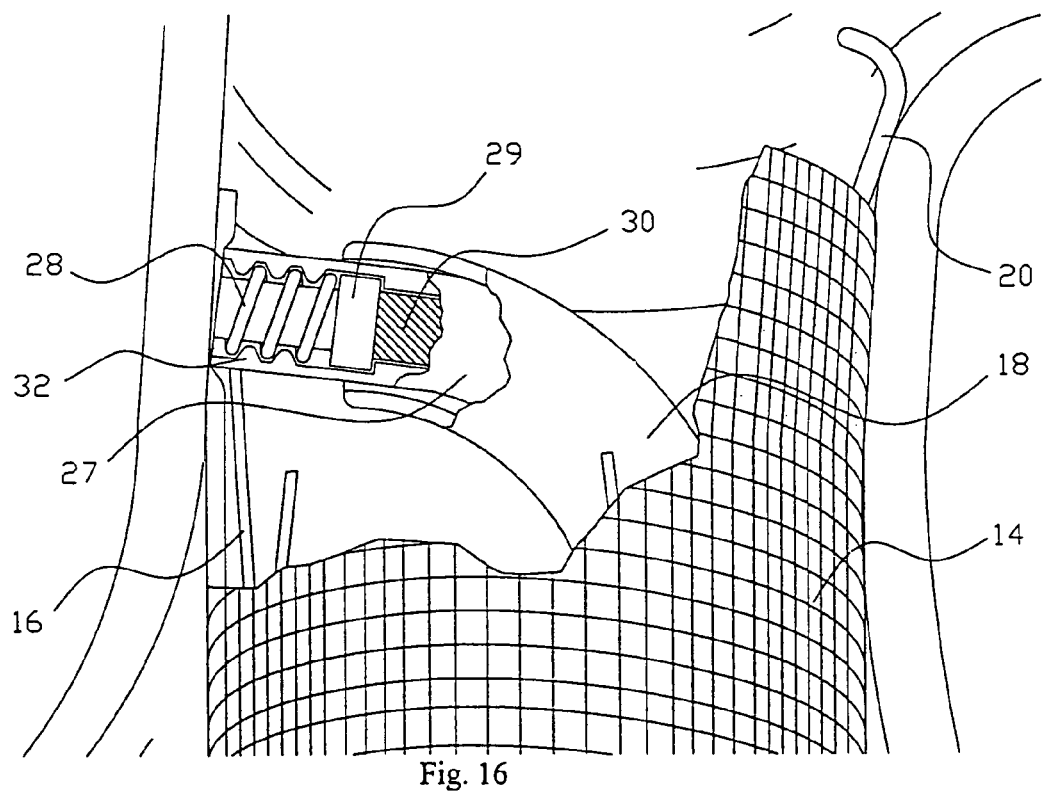
FIG. 16 is an enlarged cross-sectional view of one embodiment of the fastener applier of FIG. 14.
Figure 17:
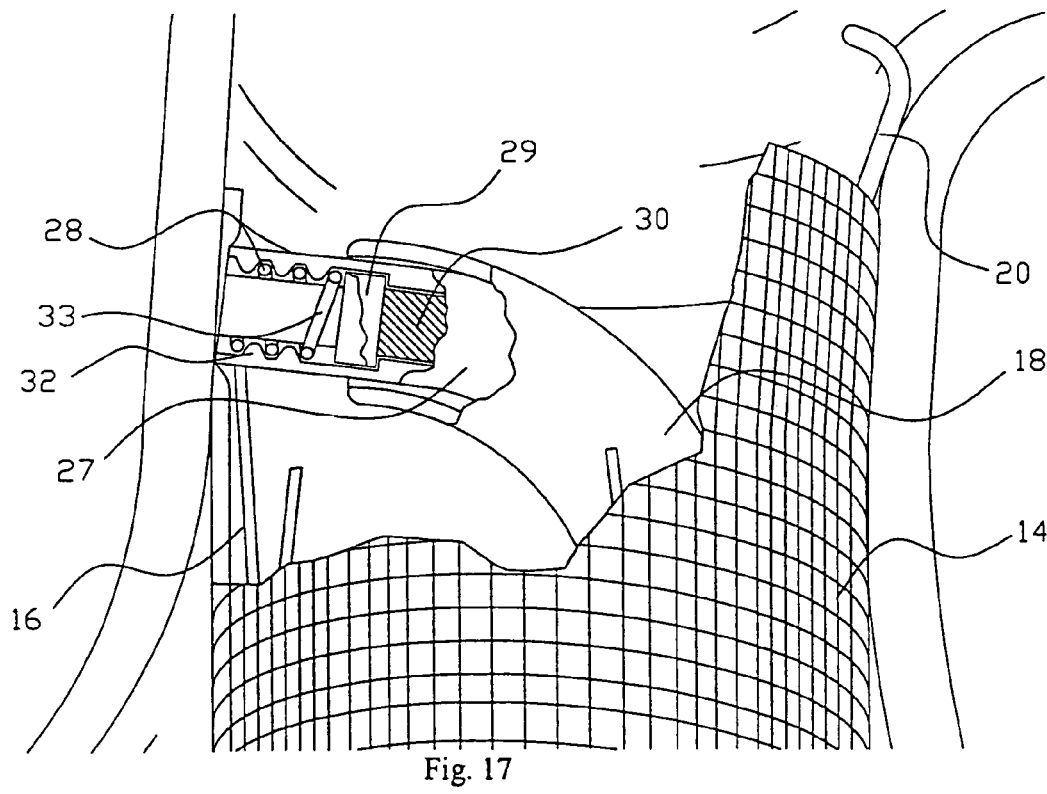
FIG. 17 is an enlarged cross-sectional view of the attachment applier showing one embodiment of the proximal end of the helical fastener and the drive mechanism.

FIG. 16 is an enlarged cross-sectional view of fastener applier 27 and directing device 18. In one embodiment of the fastener applier the helical fastener 28 is rotated via a fastener driver 29 through a drive shaft 30 that is connected to the control assembly 31. The drive shaft 30 can be made of any material that allows for both bending and rotation. The drive shaft is connected to the fastener driver 29, which engages and imparts torque to the helical fastener. FIG. 16 illustrates the coils of the helical fastener 28 engaged with internal grooves 32 within the fastener applier. It is contemplated that the grooves could be positioned along the entire length of the fastener or within a portion of its length. FIG. 17 is an enlarged cross-sectional view of the fastener applier 27 with a cross-section of the fastener driver 29 depicting one embodiment of engagement between the fastener driver and helical fastener 28. In this embodiment the proximal coil of the helical fastener is formed to produce a diagonal member 33, which crosses the diameter of the helical fastener. Similar helical fasteners are described in U.S. Pat. Nos. 5,964,772; 5,824,008; 5,582,616; and 6,296,656, the full disclosures of which are incorporated herein by reference.

Figure 18:
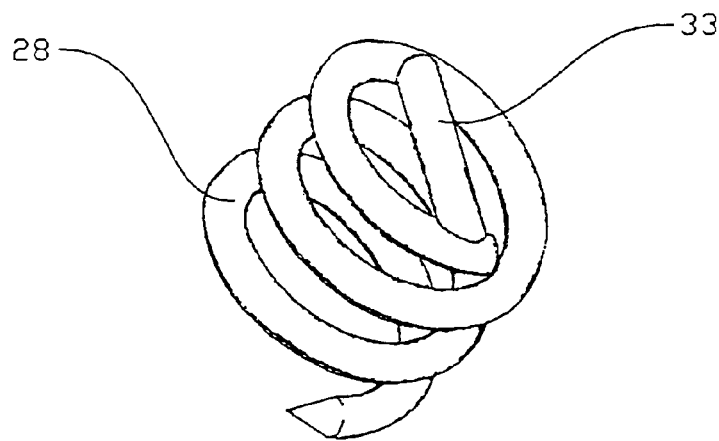
FIG. 18 is a enlarged perspective view of one embodiment of the helical fastener of FIG. 16.
Figure 19:
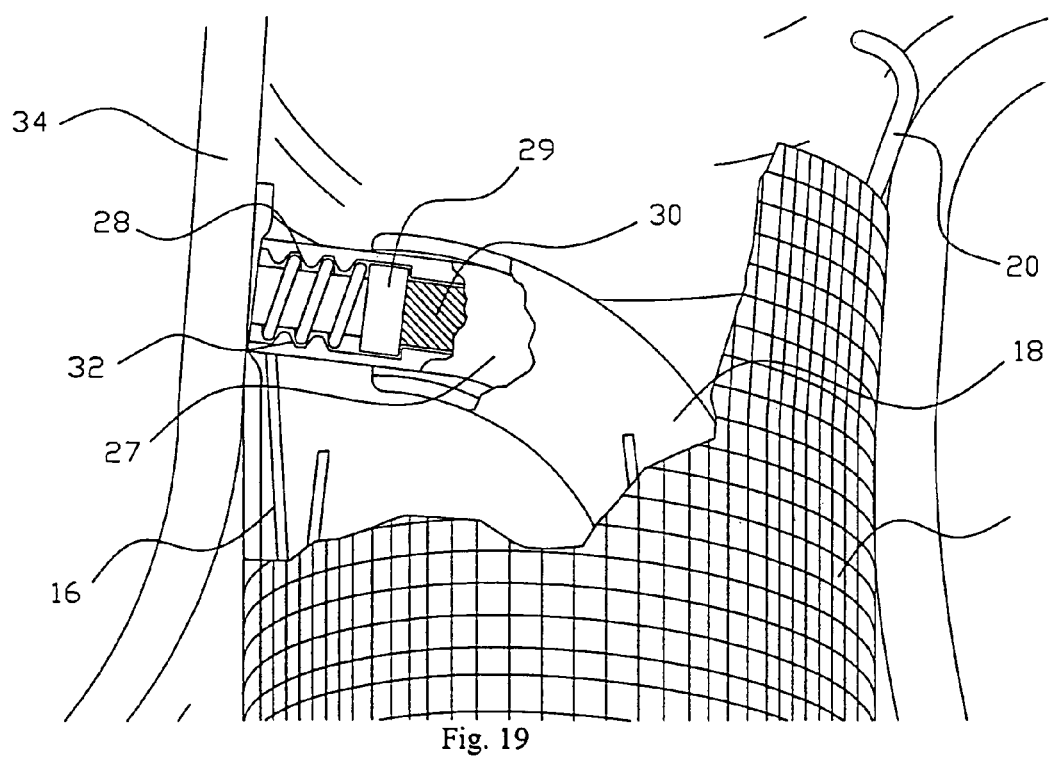
FIG. 19 is an enlarged view of the attachment applier showing one embodiment of the control assembly that activates the fastener applier.
Figure 20:
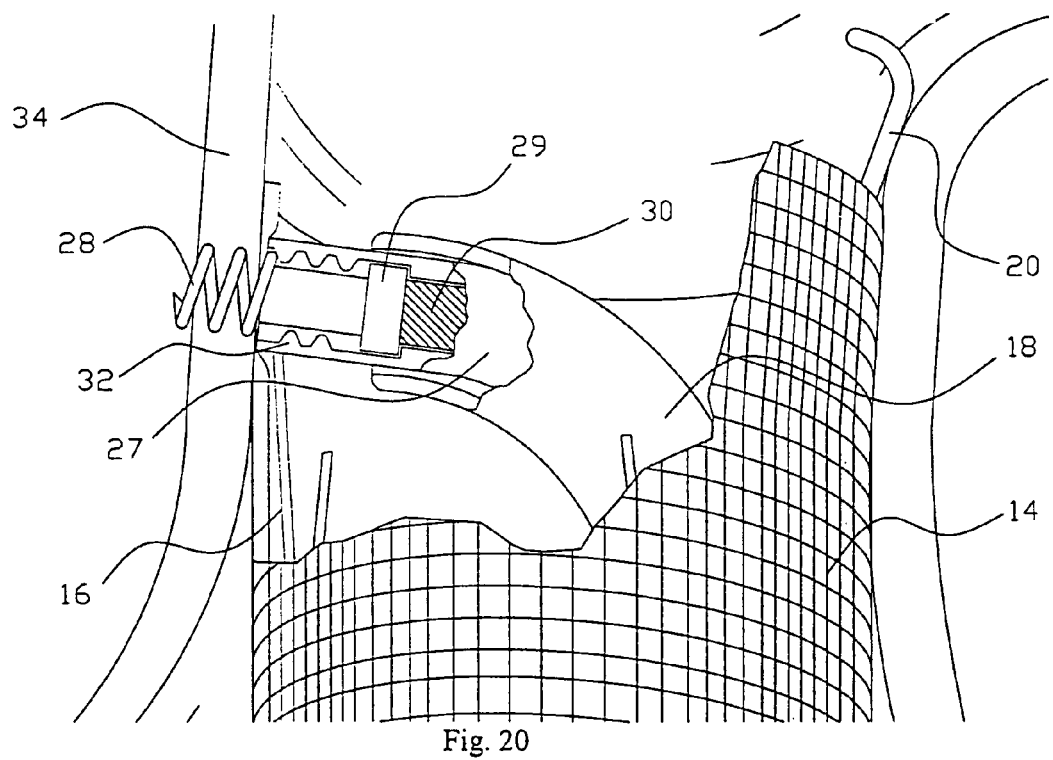
FIG. 20 is an enlarged view of the attachment applied activated with a fastener implanted into the graft and vessel wall.

FIG. 18 depicts one embodiment of the helical fastener 28 showing the diagonal member 33. FIG. 19 depicts one embodiment of the fastener applier 27 during activation of the fastener applier control assembly. Activation of the control assembly rotates the drive shaft, faster driver and helical fastener. This rotation causes the helical fastener 28 to travel within the internal grooves 32 of the fastener applier and into the graft 14 and vessel wall 34 FIG. 20. It is contemplated that the control assembly for the fastener applier could be activated mechanically, electrically, hydraulically or pneumatically.

Figure 21:
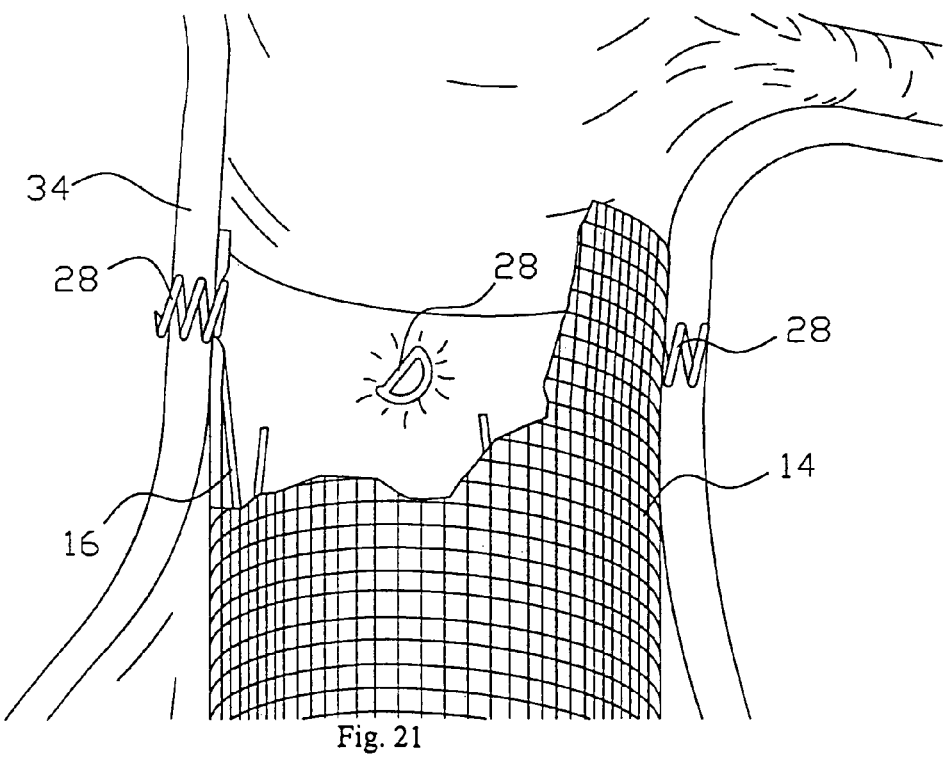
FIG. 21 is an enlarged view of the completed attachment of the proximal graft of FIG. 3 to the vessel wall with fasteners.

FIG. 21 illustrates a completed helical fastener 28 attachment of the graft 14 to the vessel wall 34. It is contemplated that one or more fasteners will be required to provide secure attachment of the graft to the vessel wall.

Figure 22:
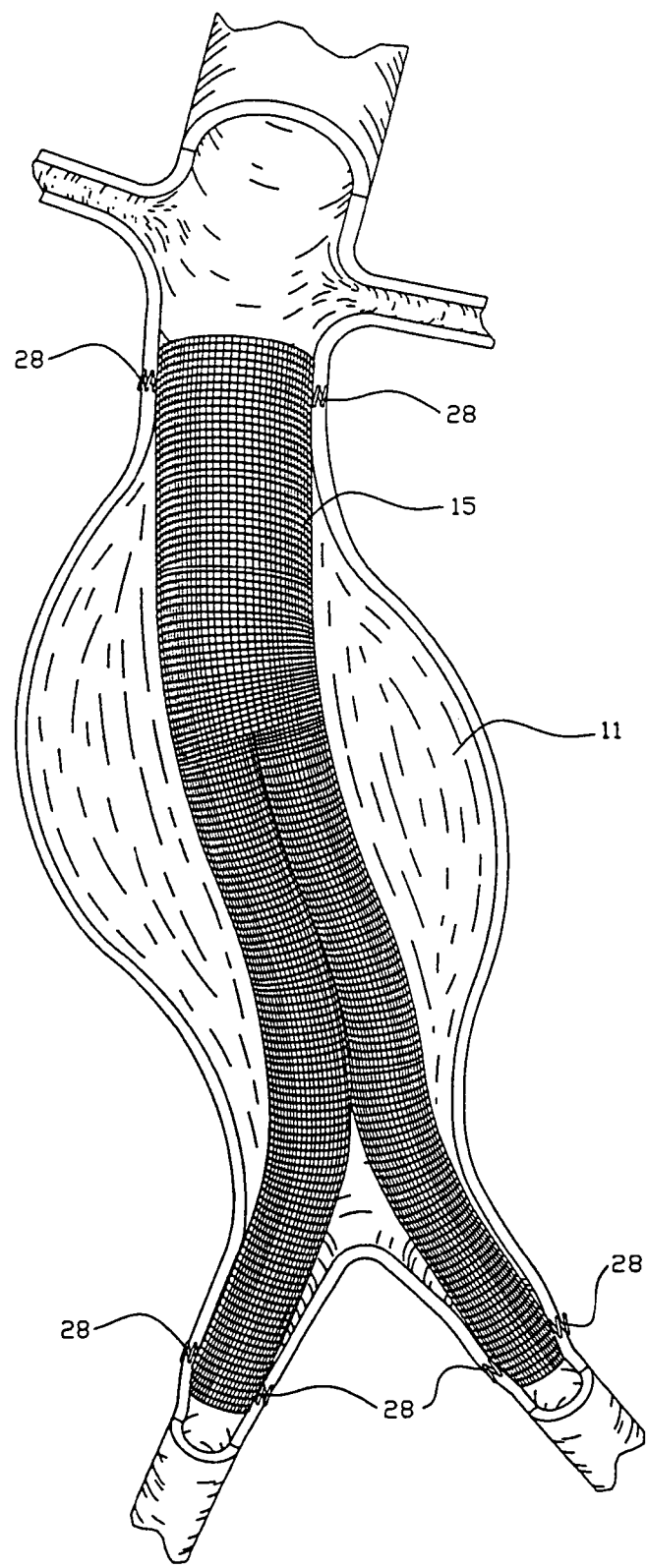
FIG. 22 is a perspective view of the graft of FIG. 4 completely attached to the vessel.

FIG. 22 illustrates a perspective view of a graft prosthesis attached to the vessel wall both proximally and distally. It is contemplated that the present invention can be used for graft attachment of both straight and bifurcated grafts 15 within the aorta and other branch vessels.

It will be appreciated that the components and/or features of the preferred embodiments described herein may be used together or separately, while the depicted methods and devices may be combined or modified in whole or in part. It is contemplated that the components of the directing device, fastener applier and helical fastener may be alternately oriented relative to each other, for example, offset, bi-axial, etc. Further, it will be understood that the various embodiments may be used in additional procedures not described herein, such as vascular trauma, arterial dissections, artificial heart valve attachment and attachment of other prosthetic device within the vascular system and generally within the body.

The preferred embodiments of the invention are described above in detail for the purpose of setting forth a complete disclosure and for the sake of explanation and clarity. Those skilled in the art will envision other modifications within the scope and sprit of the present disclosure.

What is claimed is:

1. A method for repairing a diseased or damaged section of an aorta comprising:
   (i) providing a system comprising
      at least one tissue-piercing fastener having a sharpened distal tip for piercing and penetrating tissue,
      a fastener attachment assembly sized and configured to be deployed from a remote access site to a targeted endovascular region, the fastener attachment assembly including
         an intraluminal directing device defining an access path and including a deflectable distal region, and
         at least one intraluminal fastener applier separate from the intraluminal directing device and being sized and configured for advancement into the intraluminal directing device along the access path and retrieval from the intraluminal directing device along the access path, the intraluminal fastener applier including an actuated member that is selectively operable to generate an implantation force to implant the tissue-piercing fastener by causing the sharpened distal tip to pierce and penetrate the tissue in the targeted endovascular region,
   (ii) first, introducing the intraluminal directing device separately from the intraluminal fastener applier from a remote access site to a location within a prosthesis at a target site in an aorta where the diseased or damaged section exists, thereby establishing the access path;
   (iii) and then anchoring the prosthesis at a desired fastening site on the prosthesis by advancing an intraluminal fastener applier from the remote access site into the intraluminal directing device along the access path, the intraluminal fastener carrying a single tissue-piercing fastener; by manipulating the intraluminal directing device within the prosthesis to orient the distal region with respect to the desired fastening site; and by operating the actuated member to generate the implantation force to implant the tissue-piercing fastener into tissue at the desired fastening site;
   (iv) and then separating the intraluminal fastener applier from the intraluminal directing device by retrieving the intraluminal fastener applier from the intraluminal directing device along the access path back to the remote access site;
   (v) and then anchoring the prosthesis at a different desired fastening site on the prosthesis by advancing an intraluminal fastener applier from the remote access site into the intraluminal directing device along the access path, the intraluminal fastener carrying a single tissue-piercing fastener; by manipulating the intraluminal directing device within the prosthesis to orient the distal region with respect to the different desired fastening site; and by operating the actuated member to generate the implantation force to implant the tissue-piercing fastener into tissue at the different desired fastening site;

(vi) after (v), separating the intraluminal fastener applier from the intraluminal directing device by retrieving the intraluminal fastener applier from the intraluminal directing device along the access path back to the remote access site; and (vii) repeating (v) and (vi) until a desired plurality of tissue-piercing fasteners are introduced into tissue to anchor the prosthesis, whereby the intraluminal directing device, between applications of the tissue-piercing fasteners, is manipulated into orientation with different desired fastening sites, until a plurality of tissue-penetrating fasteners are applied, one-at-a-time, in the prosthesis.

2. A method according to claim 1
wherein the prosthesis includes at least one self-expanding scaffold, and
wherein (ii) comprises releasing the prosthesis from constraint to permit the at least one scaffold of the prosthesis to self-expand at the target site.

3. A method according to claim 1
wherein the prosthesis includes at least one malleable scaffold, and
wherein (ii) comprises applying a radially expansive force within the prosthesis to cause expansion of the at least one scaffold.

4. A method according to claim 1
wherein at least one of the tissue-piercing fasteners comprises a helical tissue-piercing fastener.

5. A method according to claim 1
wherein at least one of the tissue-piercing fasteners comprises a fastener that pierces tissue in response to rotation; and
wherein (iii) and/or (v) includes rotating the fastener with a rotary driver.

6. A method according to claim 1
wherein the desired plurality of tissue-piercing fasteners are introduced in a circumferentially spaced-apart pattern to anchor the prosthesis.

7. A method according to claim 1
wherein at least one of (iii) and (v) includes rotating the intraluminal directing device and/or deflecting the distal region.

8. A method according to claim 1
wherein the intraluminal directing device includes a passage, and
wherein (iii) and (v) includes introducing an intraluminal fastener applier to the desired fastening site through the passage.

9. A method according to claim 8
wherein the passage comprises an interior lumen.

* * * * *